United States Patent
Fischer et al.

(10) Patent No.: US 6,994,546 B2
(45) Date of Patent: *Feb. 7, 2006

(54) LIGHT CURING DEVICE WITH DETACHABLE POWER SUPPLY

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 270 days.

This patent is subject to a terminal disclaimer.

(21) Appl. No.: 10/324,596

(22) Filed: Dec. 18, 2002

(65) Prior Publication Data

US 2004/0121280 A1 Jun. 24, 2004

(51) Int. Cl.
*A61C 1/00* (2006.01)

(52) U.S. Cl. ....................................................... 433/29
(58) Field of Classification Search .................. 433/29; 362/119; 250/504 H
See application file for complete search history.

(56) References Cited

U.S. PATENT DOCUMENTS

| | | |
|---|---|---|
| 3,310,358 A | 3/1967 | Marcatili |
| 3,704,928 A | 12/1972 | Coombs et al. |
| 3,930,149 A | 12/1975 | French |

(Continued)

FOREIGN PATENT DOCUMENTS

WO       WO 99/35995       7/1999

OTHER PUBLICATIONS

*3M Curing Light XL3000 (Project 95–23), Section 2b of DIS #47* (Jan. 23, 2002).
"Acta Curing Light" www.amadent.com (Jan. 23, 2002).
"All–Cure", www.all–cure.com (Jan. 23, 2002).
"ARC Light IIM", Air Techniques, Inc.
"Bellini X Ray", www.bellinixray.com (Jan. 23, 2002).
"DENTAMERICA–Litex", www.dentamerica.com (Jan. 23, 2002).
"Elipar FreeLight Curing Light", 3M ESPE, cms.3m.com (Jan. 23, 2002).
"Elipar Highlight Curing Light (Project 97–22)", ESPE America, Inc. (Jan. 23, 2002).
"Excelite", TOESCO.
"Hilux 350 Curing Light (Project 97–34)", First Medica, Inc. (Jan. 23, 2002).
"Just Cure It", Air Tecniques, Inc. (Jan. 25, 2002).
*Lurna 8™*, www.luma–lite.com (Jan. 30, 2001).
*LurnaCure Cordless Curing Light (Project 01–16), Product Evaluations DIS 64* (Jan. 23, 2002).

(Continued)

*Primary Examiner*—Cary E. O'Connor
(74) *Attorney, Agent, or Firm*—Workman Nydegger (57) ABSTRACT

The light curing devices of the invention are configured with a light applicator and one or more detachable power supply units. The light applicator is configured to emit radiant energy that is suitable to cure photo-sensitive compounds. The light applicator is also configured to be detached from the detachable power supply and to be autoclaved. The detachable power supply units are configured to provide power to the light applicator and may comprise a power cord or a battery pack that is configured in size and shape to be held within the holding slot of a holding tray, an example of which is a standard dental hand piece holding tray.

15 Claims, 5 Drawing Sheets

U.S. PATENT DOCUMENTS

| | | |
|---|---|---|
| 4,184,196 A | 1/1980 | Moret |
| 4,221,994 A | 9/1980 | Friedman et al. |
| 4,229,658 A | 10/1980 | Gonser |
| 4,245,890 A | 1/1981 | Hartman et al. |
| 4,266,535 A | 5/1981 | Moret |
| 4,281,366 A | 7/1981 | Wurster et al. ............... 362/32 |
| 4,309,617 A | 1/1982 | Long |
| 4,348,180 A | 9/1982 | Schuss |
| 4,392,827 A | 7/1983 | Martin |
| 4,522,594 A | 6/1985 | Stark et al. |
| 4,611,992 A | 9/1986 | Lokken |
| 4,666,405 A | 5/1987 | Ericson |
| 4,666,406 A | 5/1987 | Kanca, III .................. 433/229 |
| 4,682,950 A | 7/1987 | Dragan |
| 4,698,730 A | 10/1987 | Sakai et al. |
| 4,733,937 A | 3/1988 | Lia et al. |
| 4,836,782 A | 6/1989 | Gonser |
| 4,935,665 A | 6/1990 | Murata |
| 4,948,215 A | 8/1990 | Friedman |
| 4,963,798 A | 10/1990 | McDermott ................. 315/312 |
| 4,992,045 A | 2/1991 | Beisel |
| 5,013,144 A | 5/1991 | Silverglate et al. |
| 5,013,240 A | 5/1991 | Bailey et al. |
| 5,017,140 A | 5/1991 | Ascher |
| 5,043,634 A | 8/1991 | Rothwell, Jr. et al. |
| 5,071,222 A | 12/1991 | Laakmann et al. |
| 5,115,761 A | 5/1992 | Hood ......................... 118/641 |
| 5,123,845 A | 6/1992 | Vassiliadis et al. ......... 433/215 |
| 5,139,495 A | 8/1992 | Daikuzono ................... 606/17 |
| 5,161,879 A | 11/1992 | McDermott ................. 362/206 |
| 5,275,564 A | 1/1994 | Vassiliadis et al. ......... 433/226 |
| 5,285,318 A | 2/1994 | Gleckman |
| 5,288,231 A | 2/1994 | Kuehn et al. |
| 5,290,169 A | 3/1994 | Friedman et al. |
| 5,312,249 A | 5/1994 | Kennedy |
| 5,328,368 A | 7/1994 | Lansing et al. ............. 433/116 |
| 5,348,552 A | 9/1994 | Nakajima et al. ............. 606/13 |
| 5,371,826 A | 12/1994 | Friedman |
| 5,382,799 A | 1/1995 | May |
| 5,388,988 A | 2/1995 | Goisser et al. |
| 5,397,892 A | 3/1995 | Abdelqader |
| 5,415,543 A | 5/1995 | Rozmajzl, Jr. ............... 433/29 |
| 5,420,768 A | 5/1995 | Kennedy .................... 362/119 |
| D361,382 S | 8/1995 | Brunsell et al. ........... D24/177 |
| 5,448,323 A | 9/1995 | Clark et al. |
| 5,457,611 A | 10/1995 | Verderber ................... 362/572 |
| 5,485,317 A | 1/1996 | Perissinotto et al. |
| 5,521,392 A | 5/1996 | Kennedy et al. |
| 5,527,261 A | 6/1996 | Monroe et al. |
| 5,616,141 A | 4/1997 | Cipolla ........................ 606/15 |
| 5,634,711 A | 6/1997 | Kennedy et al. ............. 362/119 |
| 5,660,461 A | 8/1997 | Ignatius et al. |
| 5,669,769 A * | 9/1997 | Disel ........................... 433/29 |
| D385,051 S | 10/1997 | Wu ................................ D26/2 |
| D385,630 S | 10/1997 | Lieb et al. ................. D24/177 |
| 5,698,866 A | 12/1997 | Doiron et al. |
| 5,711,665 A | 1/1998 | Adam et al. |
| 5,733,029 A | 3/1998 | Monroe |
| 5,749,724 A | 5/1998 | Cheng |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott |
| 5,791,898 A | 8/1998 | Maissami |
| 5,797,740 A | 8/1998 | Lundvik ...................... 433/29 |
| 5,803,729 A | 9/1998 | Tsimerman ................. 433/29 |
| 5,880,839 A | 3/1999 | Ishizuka et al. |
| 5,885,082 A | 3/1999 | Levy |
| 5,905,268 A | 5/1999 | Garcia et al. |
| 5,908,294 A | 6/1999 | Schick et al. .................. 433/29 |
| 5,908,295 A | 6/1999 | Kawata ........................ 433/29 |
| 5,912,470 A | 6/1999 | Eibofner et al. ........ 250/504 H |
| 5,921,777 A | 7/1999 | Dorman |
| 5,971,755 A | 10/1999 | Liebermann et al. |
| 5,975,895 A | 11/1999 | Sullivan |
| 6,001,058 A * | 12/1999 | Sano et al. .................. 600/132 |
| 6,008,264 A | 12/1999 | Ostler et al. |
| 6,019,482 A | 2/2000 | Everett |
| 6,019,599 A | 2/2000 | Völcker et al. |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu ............................ 362/249 |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,089,740 A | 7/2000 | Forehand et al. |
| 6,095,661 A | 8/2000 | Lebens et al. |
| 6,095,812 A | 8/2000 | Senn et al. ................... 433/29 |
| 6,099,520 A | 8/2000 | Shimoji |
| 6,102,696 A | 8/2000 | Osterwalder et al. ......... 433/29 |
| 6,103,203 A | 8/2000 | Fischer |
| 6,123,545 A | 9/2000 | Eggler et al. |
| 6,155,823 A | 12/2000 | Nagel |
| 6,159,005 A | 12/2000 | Herold et al. |
| 6,200,134 B1 | 3/2001 | Kovac et al. |
| 6,208,788 B1 | 3/2001 | Nosov |
| 6,270,343 B1 | 8/2001 | Martin |
| 6,280,187 B1 | 8/2001 | Slone |
| 6,282,013 B1 | 8/2001 | Ostler et al. |
| 6,318,996 B1 | 11/2001 | Melikechi et al. ............ 433/29 |
| 6,322,358 B1 | 11/2001 | Senn et al. ................... 433/29 |
| 6,325,623 B1 | 12/2001 | Melnyk et al. ............... 433/29 |
| 6,328,456 B1 | 12/2001 | Mize |
| 6,331,111 B1 | 12/2001 | Cao ........................... 433/29 |
| 6,361,192 B1 | 3/2002 | Fussell et al. |
| 6,361,489 B1 | 3/2002 | Tsai |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 | 7/2002 | Adam et al. |
| 6,439,888 B1 | 8/2002 | Boutoussov et al. |
| 6,465,961 B1 | 10/2002 | Cao |
| 6,468,077 B1 | 10/2002 | Melikechi et al. ............ 433/29 |
| 6,478,447 B2 | 11/2002 | Yen |
| 6,482,004 B1 | 11/2002 | Senn et al. ................... 433/29 |
| 6,485,301 B1 | 11/2002 | Gemunder et al. |
| 6,511,317 B2 | 1/2003 | Melikechi et al. ............ 433/29 |
| 6,511,321 B1 | 1/2003 | Trushkowsky et al. |
| 6,514,075 B1 | 2/2003 | Jacob |
| 6,611,110 B1 | 8/2003 | Fregoso |
| 6,692,251 B1 | 2/2004 | Logan et al. |
| 6,692,252 B2 | 2/2004 | Scott |
| 6,709,128 B2 | 3/2004 | Gordon et al. |
| 6,719,558 B2 | 4/2004 | Cao |
| 6,719,559 B2 | 4/2004 | Cao |
| 6,755,648 B2 | 6/2004 | Cao |
| 6,755,649 B2 | 6/2004 | Cao |
| 2001/0038992 A1 | 11/2001 | Otsuka |
| 2001/0046652 A1 | 11/2001 | Ostler et al. |
| 2001/0055451 A1 | 12/2001 | Kuhara et al. |
| 2002/0073921 A1 | 6/2002 | Russell et al. |
| 2002/0085372 A1 | 7/2002 | Lehrer |
| 2002/0093833 A1 | 7/2002 | West |
| 2002/0102513 A1 | 8/2002 | Plank |
| 2002/0115037 A1 | 8/2002 | Cao ........................... 433/29 |
| 2002/0133970 A1 | 9/2002 | Gordon et al. |
| 2002/0147383 A1 | 10/2002 | Weber et al. |
| 2002/0163317 A1 | 11/2002 | Cao ........................... 315/291 |

| | | | | | | |
|---|---|---|---|---|---|---|
| 2002/0167283 A1 | 11/2002 | Cao | 315/291 | 2003/0148242 A1 | 8/2003 | Fischer et al. |
| 2002/0168306 A1 | 11/2002 | Cao | | 2003/0152885 A1 | 8/2003 | Dinh |
| 2002/0168603 A1 | 11/2002 | Cao | 433/29 | 2003/0186195 A1 | 10/2003 | Comfort et al. |
| 2002/0168604 A1 | 11/2002 | Cao | 433/29 | 2003/0215766 A1 | 11/2003 | Fischer et al. |
| 2002/0168605 A1 | 11/2002 | Cao | 433/29 | 2003/0218880 A1 | 11/2003 | Brukilacchio |
| 2002/0168606 A1 | 11/2002 | Cao | 433/29 | 2003/0219693 A1 | 11/2003 | Cao |
| 2002/0168607 A1 | 11/2002 | Cao | 433/29 | 2003/0219694 A1 * | 11/2003 | Bianchetti et al. ............ 433/29 |
| 2002/0168608 A1 | 11/2002 | Cao | 433/29 | 2003/0235800 A1 | 12/2003 | Qadar |
| 2002/0172912 A1 | 11/2002 | Cao | 433/29 | 2004/0033033 A1 | 2/2004 | Hoshino et al. |
| 2002/0172913 A1 | 11/2002 | Cao | 433/29 | | | |
| 2002/0172914 A1 | 11/2002 | Cao | 433/29 | | | |
| 2002/0172915 A1 | 11/2002 | Cao | 433/29 | | | |
| 2002/0172916 A1 | 11/2002 | Cao | 433/29 | | | |
| 2002/0172917 A1 | 11/2002 | Cao | 433/29 | | | |
| 2002/0175352 A1 | 11/2002 | Cao | 257/258 | | | |
| 2002/0175628 A1 | 11/2002 | Cao | 315/56 | | | |
| 2002/0177095 A1 | 11/2002 | Cao | 433/29 | | | |
| 2002/0177096 A1 | 11/2002 | Cao | 433/29 | | | |
| 2002/0177099 A1 | 11/2002 | Cao | 433/29 | | | |
| 2002/0180368 A1 | 12/2002 | Cao | 315/149 | | | |
| 2002/0181947 A1 | 12/2002 | Cao | 392/409 | | | |
| 2002/0182561 A1 | 12/2002 | Cao | 433/29 | | | |
| 2002/0182562 A1 | 12/2002 | Cao | 433/29 | | | |
| 2002/0187454 A1 | 12/2002 | Melikechi et al. | | | | |
| 2002/0187455 A1 | 12/2002 | Melikechi et al. | | | | |
| 2002/0190659 A1 | 12/2002 | Cao | 315/149 | | | |
| 2002/0190660 A1 | 12/2002 | Cao | 315/149 | | | |
| 2002/0197582 A1 | 12/2002 | Cao | 433/29 | | | |
| 2003/0001507 A1 | 1/2003 | Cao | 315/56 | | | |
| 2003/0036031 A1 | 2/2003 | Lieb et al. | | | | |
| 2003/0038291 A1 | 2/2003 | Cao | 257/81 | | | |
| 2003/0039119 A1 | 2/2003 | Cao | 362/227 | | | |
| 2003/0039120 A1 | 2/2003 | Cao | 362/227 | | | |
| 2003/0039122 A1 | 2/2003 | Cao | 362/294 | | | |
| 2003/0040200 A1 | 2/2003 | Cao | 438/800 | | | |
| 2003/0081430 A1 | 5/2003 | Becker | | | | |
| 2003/0133203 A1 | 7/2003 | McLean et al. | | | | |
| 2003/0133298 A1 | 7/2003 | Cao | | | | |
| 2003/0142413 A1 | 7/2003 | McLean et al. | | | | |
| 2003/0147254 A1 | 8/2003 | Yoneda et al. | | | | |
| 2003/0147258 A1 | 8/2003 | Fischer et al. | | | | |

OTHER PUBLICATIONS

"LUXoMAX the Latest News from Akeda Dental", Akeda Dental A/S, www.akeda.dk (Oct. 1, 2001).

"NRG L.E.D. Curing Light", Dentsply Caulk (2001).

"Optilux 500 Polymerization Units (Project 96–33)", Demetron Research Corporation/Kerr (Jan. 23, 2002).

"Optilux 501 Polymerization Unit (Project 00–03)", Kerr/Demetron (Jan. 23, 2002).

"RemeCure CL 15", Remedent, www.remedent.com (Jan. 23, 2002).

"Resin Curing Lights" Clinical Research Associates Newsletter (Mar. 1996).

"Resin Curing Lights: What You Should Know", Contemporary Esthetics and Restorative Practice, p. 36 (Nov. 2001).

"Savings on Curing Lights from Lone Star Dental Corp.", Lone Star Dental Corp., www.dentequip.com (Jan. 23, 2002).

"Starlight" Mectron Medical Technology.

"The Power PAC", American Dental Technologies, www.americandentaltech.com (Jan. 23, 2002).

"Variable Intensity Polymerizer Light Curing Unit (VIP) (Project 99–14)", BISCO, Inc. (Jan. 23, 2002).

"VivaluxII Cordless Polymerization Unit (Project 96–39)", Ivoclar North America (Jan. 23, 2002).

"ZAP Dual Curing Light (Project 01–26)", CSM–Dental (Denmark)/Soft–core Texas, Inc. (Jan. 23, 2002).

* cited by examiner

LIGHT CURING DEVICE WITH DETACHABLE POWER SUPPLY

BACKGROUND OF THE INVENTION

1. The Field of the Invention

The present invention is in the field of light curing devices and, more particularly, to dental light curing devices.

2. The Relevant Technology

In the field of dentistry, dental cavities are often filled and/or sealed with photosensitive compounds that are cured when they are exposed to radiant energy, such as visible light. These compounds, commonly referred to as light curable compounds, are placed within dental preparations or onto dental surfaces where they are subsequently irradiated by a light curing dental device.

Existing light curing devices are configured to emit adequate light from one or more light sources into a patient's mouth and in a manner that is suitable to cure the light curable compounds. Typically, at least a portion of the light curing device is inserted within the patient's mouth proximate a dental preparation to help ensure the light is dispersed at the desired location. Inserting the light curing device with the patient's mouth, however, necessitates that the light curing device is sterilized between uses.

Sterilizing the light curing device between uses is a tedious task that is complicated by the size and shape of exiting light curing devices. For instance, the battery pack or power cord of existing light curable devices makes it somewhat awkward to move the light curing devices to a sterilizing station, thereby complicating the sterilizing process.

One existing method for maintaining a sterile light curing device, which is disclosed in U.S. Pat. No. 6,102,696, issued to Osterwalder et al., includes the use of a transparent sleeve that is placed over the portion of the light curing device that is inserted within the patient's mouth. Between uses, the transparent sleeve can then be replaced with a new sterile sleeve. The plastic sleeve, however, can be difficult to position and replace and is not necessarily easier than sanitizing the light curing device. The plastic sleeve may also create undesired optical dispersion of the light.

Another problem experienced with existing light curing devices is that the attached power cords make them somewhat inconvenient to freely transport between different locations. For instance, it is somewhat awkward and hazardous to carry a light curing device from room to room when the device has a dangling cord. It can also be time consuming and undesirable to have to ravel the cord up before moving the device.

Although battery powered light curing devices are more mobile than light curing it is also somewhat limited. In devices having cords, it can be difficult to find an adequate location to temporarily store the battery pack while the light curing device is separated from the battery pack. This can be a problem because the battery pack may become misplaced, lost, or even worse, the battery pack may be unintentionally dropped and damaged.

Yet another problem with existing light curing devices is that they are typically sold as single integrated units. This can be a problem when a portion of the light curing device becomes damaged or otherwise becomes nonfunctional, such as when the light-generating source burns out in which case, the entire light curing device must be replaced. This is undesirable from a practitioner's perspective because of the cost required to buy a new device. The integration of existing light curing devices is also undesirable in certain circumstances because this essentially limits the functionality of the light curing devices to the inherent characteristics of the integrated components. Integration prevents the components from being interchanged to utilize the different attributes and functionality of the alternate components.

Accordingly, in view of the foregoing, there is currently a need in the art for improved light curing devices.

SUMMARY OF PRESENTLY PREFERRED EMBODIMENTS

Briefly summarized, the present invention is directed to improved light curing devices that are capable of being easily sterilized, transported and that are capable of utilizing detachable components.

According to one embodiment, the light curing devices of the invention includes detachable power supply units and light applicators that are detachably connectable. The detachable power supply unit may include a detachable battery pack or a detachable power cord that is configured to receive power from a remote source, such as a wall outlet, a remote battery, or a remote generator.

The detachable power supply unit is preferably configured in size and shape to be securely held within the holding slot of a standard dental hand piece holding tray. It will be appreciated that this is useful for at least minimizing any chance a battery pack will get misplaced. This also minimizes any chance that a power cord will become tangled, tripped over, or otherwise become a nuisance when the light-applicator is moved during periods of non-use. In particular, the battery pack and/or power cord can remain securely held in a known and desirable location while the light applicator is moved to a different location or separated from the power supply unit to be cleaned or replaced.

According to another aspect of the invention, the light applicator is configured to be sterilized in an autoclave. Accordingly, between uses, the light applicator can be separated from the detachable power supply unit and sterilized in an autoclave. While the light applicator is sterilized, the detachable power supply unit can be left securely held within the holding slot of a standard hand piece holding tray.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the invention will now be provided with specific reference to figures illustrating preferred embodiments of the invention. It will be appreciated that like structures will be provided with like reference designations. To provide context for interpreting the scope of the invention, certain terms used throughout the application will now be defined.

The term "dental hand piece," as used herein, generally refers to a handheld dental device that engages rotary instruments for cutting, cleaning, polishing or otherwise treating teeth. The term "dental hand piece" is a term of art well known in the dental industry. Nonlimiting examples of dental hand pieces include high speed turbines, low speed turbines, ultrasonic devices, and 3-way syringes. Dental hand pieces are typically driven by pneumatic, electric, and ultrasonic mechanisms.

The term "dental hand piece holding tray" generally refers to a tray configured with holding slots specifically configured in shape and size for holding conventional dental hand pieces. Dental hand piece holding trays, which are well-known to those skilled in the art, are placed proximate or mounted directly to dental chairs for facilitating access to dental hand pieces held by the holding trays.

The terms "holding slot" and "holder," which are used interchangeably herein, generally refer to devices configured in size and shape to securely hold a dental hand piece. A holding slot is a typical feature of a dental hand piece holding tray.

The term "light applicator," as used herein, refers to a portion of the light curing device that is configured in size and shape to be inserted at least partially within the mouth of a patient and which is also configured to transmit, emit, direct, or otherwise apply light to a desired application site within the patient's mouth. By way of example, and not limitation, the light applicator may include a light source and corresponding light source mounting structures that are configured in size and shape to be inserted into a patient's mouth. The term "light source" includes any light generating device, including, but not limited to, a halogen bulb, a light-emitting diode (LEDs), an LED array, and combinations thereof. The light applicator may also include integral and detachable shields, lenses, and other components configured for insertion within the patient's mouth.

The terms "light-sensitive compound," "light curable compound," and "compound" are used interchangeably herein and refer to compounds that are configured to solidify or otherwise cure upon receiving appropriate radiant energy in the form of light from a light source of a light curing device.

In general, the light curing devices of the present invention, as described herein, are configured with a detachable power supply unit that is detachably connectable with a light applicator. The detachable power supply units of the invention may include battery packs and power cords that are configured in size and shape to be securely held within the holding slot of a standard dental hand piece holding tray.

Figure 1:
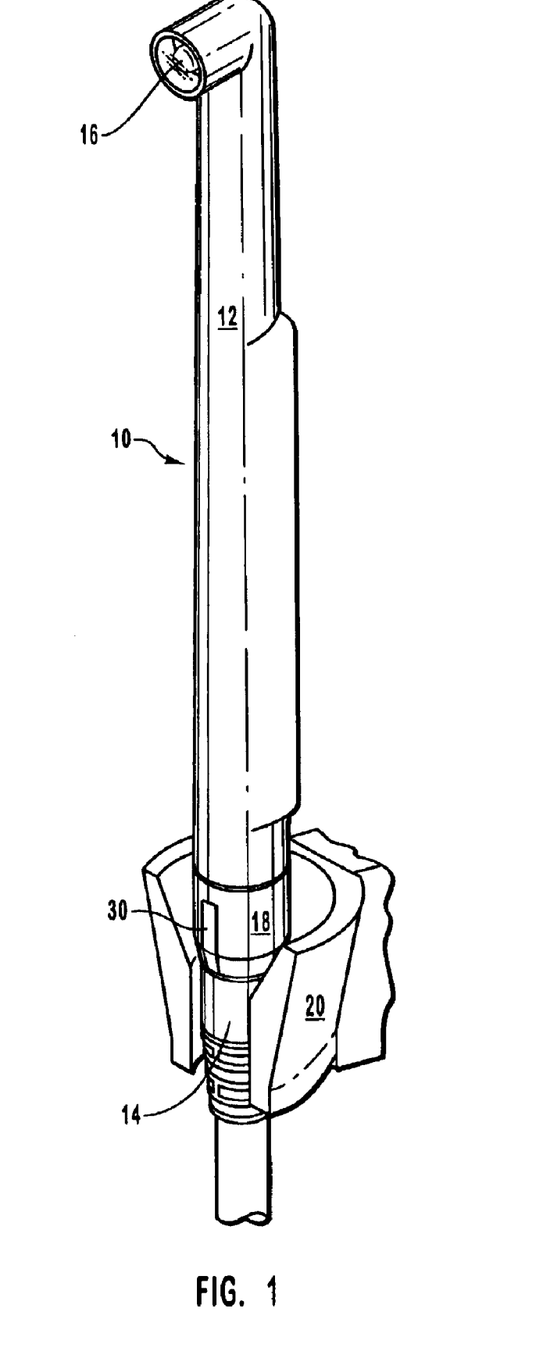
FIG. 1 illustrates a perspective view of one embodiment of the light curing device of the invention that includes a light applicator that is connected to a power cord securely held in the holding slot of a dental hand piece holding tray.

FIG. 1 illustrates one presently preferred embodiment of the light curing device 10 of the invention. As shown, the light curing device 10 includes a light applicator 12 and a detachable power supply unit 14 that are connected together. The electrical and mechanical coupling between the light applicator and the detachable power supply unit 14 will be discussed below in more detail in reference to FIGS. 2 and 3.

The light applicator 12 is configured to generate and emit light suitable for curing light curable compounds. This may be accomplished, for example, with an LED 16 or any other suitable light-generating source disposed in the light curing device 10. During normal use, the generated light is emitted from a top portion of the light applicator 12 and into the mouth of a patient. As shown, the light applicator 12 is configured in shape and size to be inserted at least partially into the mouth of a patient.

During normal use, the light applicator 12 is preferably sanitized between uses to avoid communicating diseases or other contaminating elements between patients. This may be accomplished for example by detaching the light applicator 12 from the detachable power supply unit 14 and autoclaving the light applicator 12. Accordingly, the light applicator is preferably composed of materials that can be autoclaved. The temperature of an autoclave typically reaches about 130° C. Accordingly, it is preferable for the light applicator 12 to be composed of materials that can at least withstand a temperature of 130° C. Examples of suitable materials that can use used to manufacture the shell or body of the light applicator 12 and that are autoclavable include, but are not limited to, polysulphone (PSU) and polyphenylsulphone (PPSU).

As mentioned above, the light applicator 12 is detachably connected with a detachable power supply unit 14, which may comprise a power cord 18, as shown, or a battery pack as shown and described below in more detail in reference to FIG. 4. According to one embodiment, the detachable power supply unit 14 is configured in size and shape to be held within the holding slot 20 of a standard dental hand piece holding tray, as shown. This is useful, for example, to enable the detachable power supply unit 14 to be securely held in a desired location while the light applicator 12 is detached for replacement, for cleaning, to be moved to a different station, or for any other reason.

Figure 2:
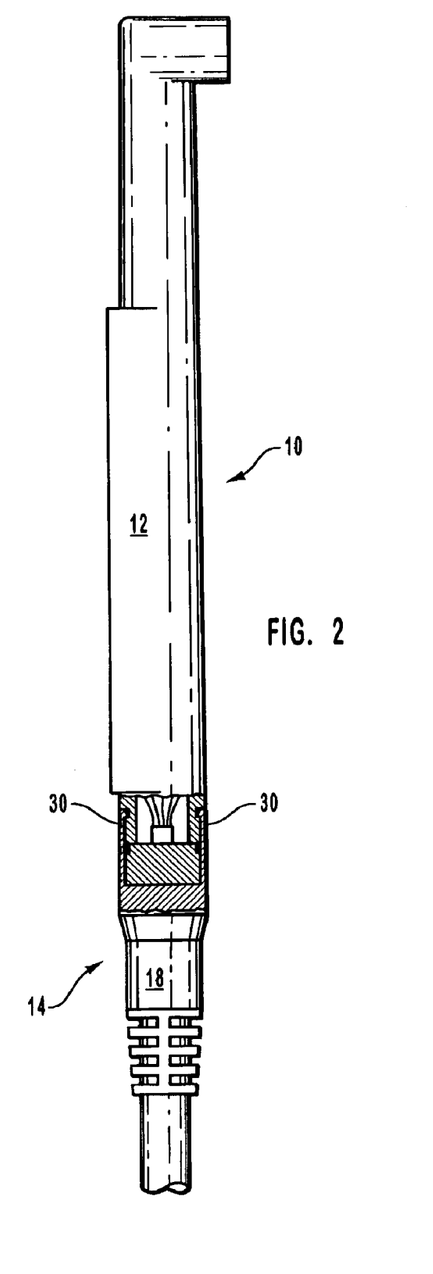
FIG. 2 illustrates a partial cross-sectional view of the light curing device of the invention that shows the detachable coupling of the light applicator and the power cord.

FIG. 2 illustrates a partial cross-sectional side view of the light curing device 10. As shown, the light applicator 12 is mechanically coupled with the detachable power supply unit 14. In the present embodiment, latches 30 mechanically secure the light applicator 12 to the detachable power supply unit 14. To remove the light applicator 12, the latches 30 can be pulled away from the light applicator 12 with a small tool or with the fingers of a practitioner.

Figure 3:
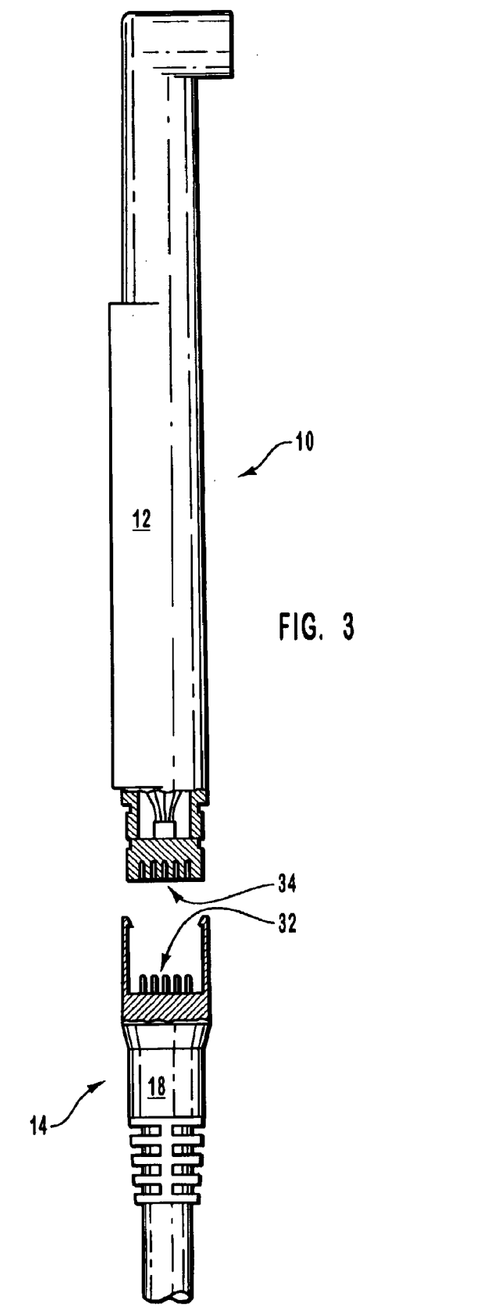
FIG. 3 illustrates a partial cross-sectional view of the light curing device of FIG. 1 that shows the light applicator detached from the power cord.

FIG. 3 illustrates another cross-sectional side view of the light curing device 10. In this embodiment, the light applicator 12 has been removed from the detachable power supply unit 14. This embodiment also illustrates how the light applicator 12 and the detachable power supply unit 14 are configured with suitable connectors to provide an electrical coupling. In particular, the detachable power supply 10 includes pins 32 that are configured to couple with the receptacles 34 formed in the light applicator 12. During use, when the light applicator 12 is coupled with the detachable power supply unit 14, electrical current is able to flow between the pins 32 and the receptacles 34 to provide power to the light curing device 10.

It will be appreciated that the type of electrical coupling between the light applicator 12 and the detachable power supply unit 14 may be modified or altered to accommodate different needs and preferences and may include any number of electrical coupling components. By way of example and not limitation, the light curing device 10 may alternatively be configured with electrical pins that are disposed on the light applicator 12 and corresponding receptacles that are disposed within the detachable power supply unit 14.

Figure 4:
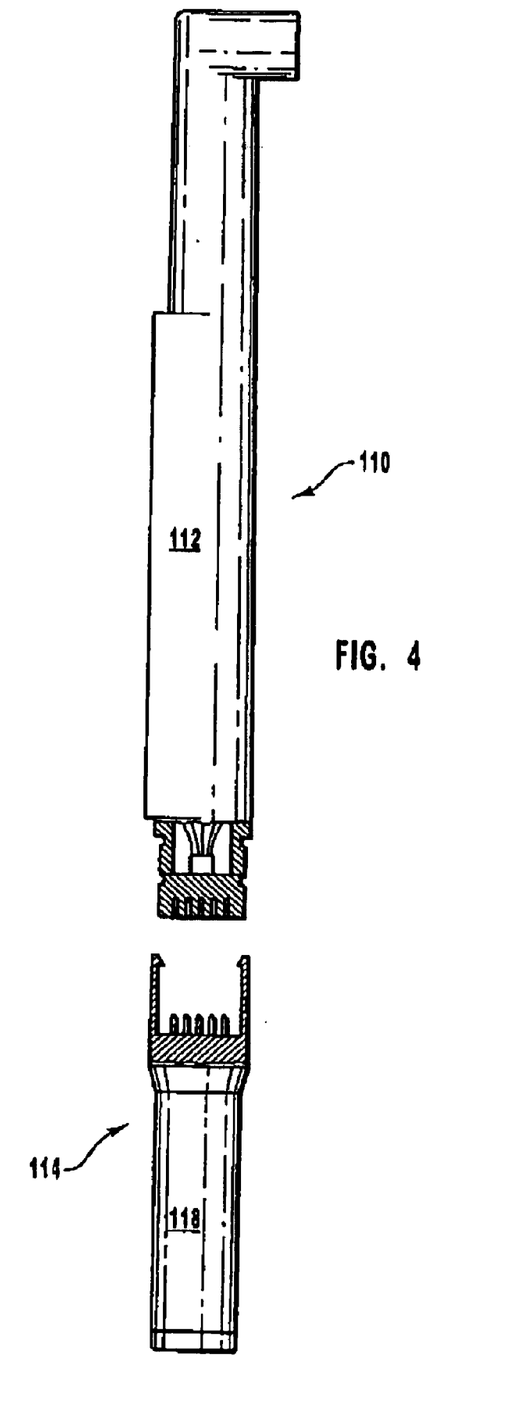
FIG. 4 illustrates a partial cross-sectional view of one embodiment of the light curing device in which the light applicator is connected to a detachable battery pack that is configured in size and shape to be held in the holding slot of a standard dental hand piece holding tray.

FIG. 4 illustrates another embodiment of the light curing device 110. In this embodiment, the light applicator 112 is configured to detachably couple with a detachable power supply unit 114 comprising a battery pack 118. Noticeably, the battery pack 118 is configured in size and shape to be held in the holding slot of a standard hand piece holding tray. As mentioned above, this is useful for enabling the detachable power supply unit 114 to be held within a designated holding slot while the light applicator 112 is temporarily detached for cleaning or for any other reason.

Figure 5:
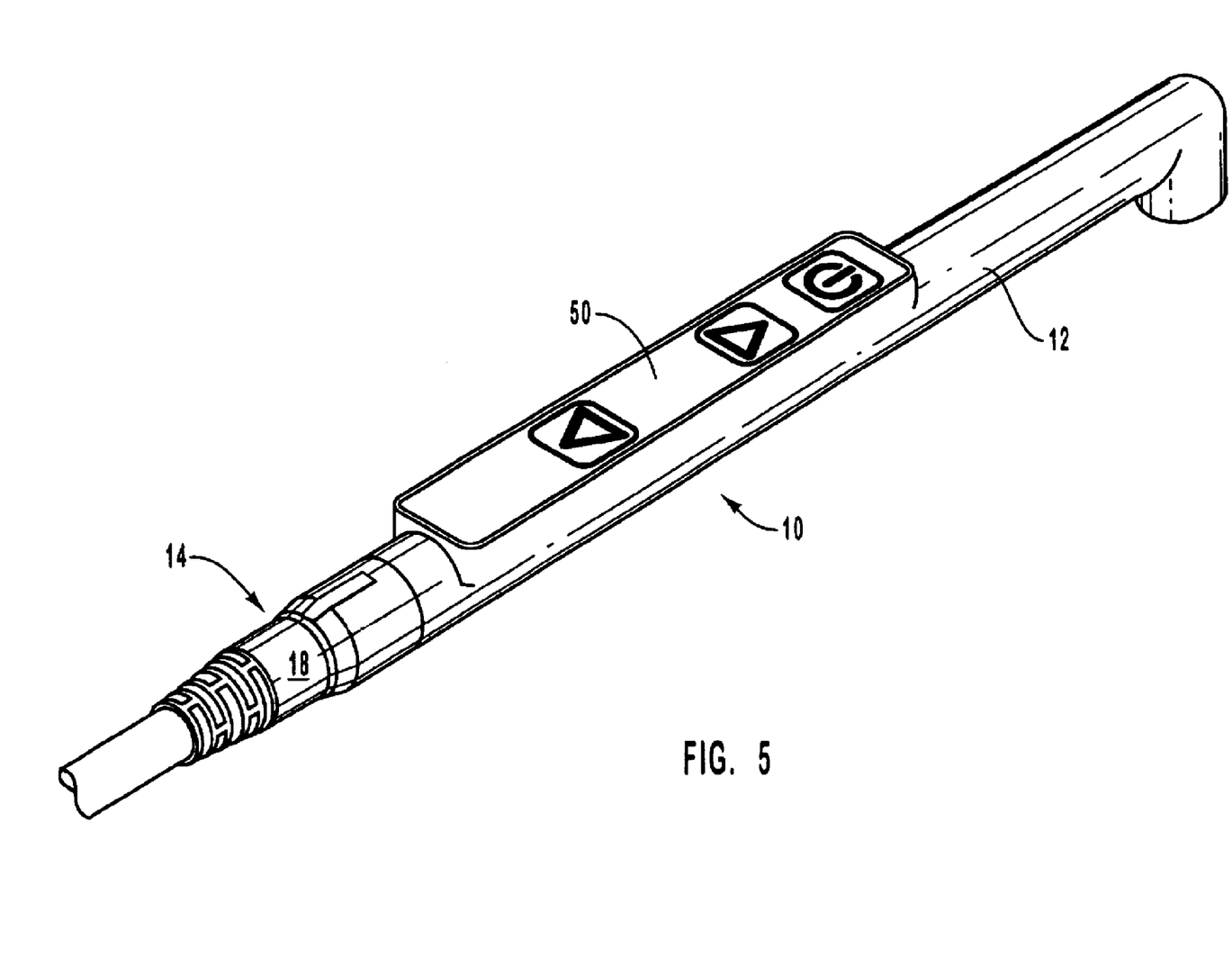
FIG. 5 illustrates a perspective view of the light curing device of FIG. 1 that shows a control panel that may be used for controlling the light curing device.

FIG. 5 illustrates a perspective view of the light curing device 10 from an angle that shows a control panel 50 disposed on the body of the light-applicator 12. The control panel 50 preferably includes control buttons that enable a user to operate the light curing device 10 with finger control. The control panel 50 may be configured to provide any desired functionality. By way of example and not limitation, the control panel 50 may enable the user to increase and decrease the duration of time in which the light curing device 10 is activated. The control panel 50 may also be used to activate and deactivate the light curing device 10.

In one embodiment, the control panel 50 is sealed to the light-applicator 12 in such a way as to protect the light-applicator 12 from water that could otherwise leak into the light-applicator 12 during cleaning. In another embodiment, the seal of the control panel 50 is sufficient to prevent steam from penetrating the electronic circuitry disposed within the light-applicator 12, such as, for example, during autoclaving.

Figure 6:
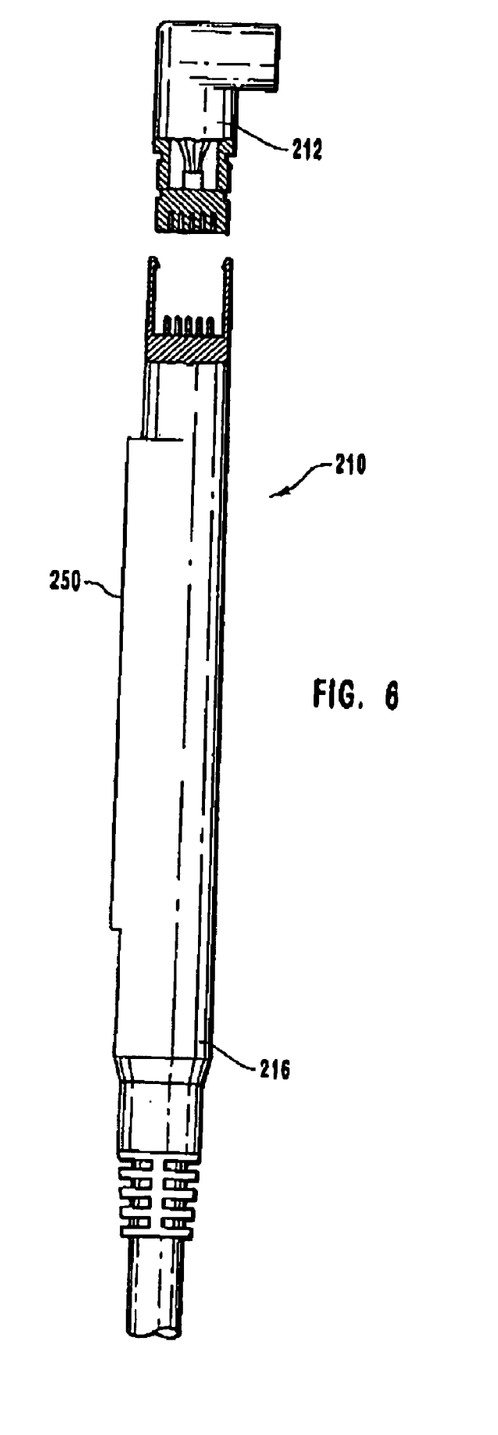
FIG. 6 illustrates a partial cross-sectional view of one embodiment of the light curing device in which the light applicator is disposed above the control panel of the light-curing device.

FIG. 6 illustrates yet another embodiment of the light curing device 210 of the invention. In this embodiment, the light applicator 212 is configured to detach from the detachable power supply unit 216 above the control panel 250. This embodiment is useful for minimizing any problems that may occur due to a bad seal during autoclaving. This embodiment is also useful for minimizing the expense that may be incurred when replacing the light-applicator 212, inasmuch as the light applicator 212 includes fewer components than in the other light applicators disclosed above. The light applicator 212 is preferably, but not necessarily, configured with sufficient length to enable the light applicator to be inserted within the patient's mouth for curing light curable compounds without requiring any portion of the detachable power supply unit 216 to be inserted within the patient's mouth. This is useful for enabling the light curing device 210 to be adequately sterilized by only autoclaving the light applicator 212, without also requiring autoclaving of the detachable power supply unit 216.

In summary, the light curing devices of the invention are configured with a light applicator and a detachable power supply unit that are detachably interconnectable. The light applicator is configured to emit light that is suitable to cure photo-sensitive compounds into the mouth of a patient and to be autoclaved. The detachable power supply unit includes a power cord or a battery pack that is configured in size and shape to be held within the holding slot of a dental hand piece holding tray so that it can remain within the holding slot while the light applicator is transported, cleaned or replaced.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A relatively light weight, hand-held dental device for curing light-curing compounds, and that is adapted for use in a system that includes a holding fray comprising one or more recesses, at least one of which is for receiving the dental device so as to hold the dental device in a convenient, generally upright fashion for easy grasping, the dental device comprising:

body means for defining a generally elongated, light-weight, slender body for enabling the dental device to be held and easily rotated into various positions when using the dental device for curing procedures in a patient's mouth, and said body means also comprising means for controlling application of power;

means, disposed at a first end of the body means, for emitting radiant energy directly to a light-curable compound within a patient's mouth, said radiant energy being suitable for curing light-curable dental compounds;

power means, disposed at a second end of the body means, for providing power to the means for emitting radiant energy, and said means for providing power also comprising means that adapts the dental device for securely sitting in an essentially elongated, upright fashion within the at least one recess of the holding tray when it is not in use; and detachment means for detachably connecting the means for emitting radiant energy to the power means so that the means for emitting radiant energy can be selectively detached from the body means for autoclaving.

2. A dental device as recited in claim 1, comprising at least one of polysulphone or polyphenylsulphone.

3. A dental device as recited in claim 1, said means for controlling application of power comprising a control panel with controls for operating the means for emitting radiant energy.

4. A dental device as recited in claim 1, wherein the control panel is disposed on said detachment means.

5. A dental device as recited in claim 1, wherein said detachment means comprises latches configured to mechanically latch the power means to said body means.

6. A dental device as recited in claim 1, wherein said means for emitting radiant energy comprises at least one LED or LED array.

7. A dental device as recited in claim 1, wherein said power means comprises a power cord.

8. A dental device as recited in claim 7, wherein the power cord is configured to receive power from a remote power supply.

9. A dental device as recited in claim 1, wherein said power means comprises a battery pack.

10. A dental device as recited in claim 1, wherein said power means includes a plurality of detachable power supply units configured to provide power to the light applicator and that are interchangeable with each other.

11. A dental device as recited in claim 1, wherein the dental device is configured to withstand temperatures of at least 130° C. during autoclaving.

12. A dental device as recited in claim 1, said means for controlling application of power comprising a control panel with controls for operating the dental device, the control panel being sealed to the body means.

13. A dental device as defined in claim 1, wherein said detachment means is situated between said means for emitting radiant energy and said body means so that said means for emitting radiant energy is detachable from both said body means and said power means for autoclaving separate therefrom.

14. A dental device as defined in claim 1, wherein said detachment means is situated between said body means and said power means so that said body means and said means for emitting radiant energy are detachable as a single unit for autoclaving separate from said power means.

15. A dental device as defined in claim 1, wherein said detachment means includes electrical pins disposed on the power means and corresponding electrical receptacles on said body means.

* * * * *

UNITED STATES PATENT AND TRADEMARK OFFICE
CERTIFICATE OF CORRECTION

PATENT NO. : 6,994,546 B2
APPLICATION NO. : 10/324596
DATED : February 7, 2006
INVENTOR(S) : Dan E. Fischer et al.

It is certified that error appears in the above-identified patent and that said Letters Patent is hereby corrected as shown below:

Title Page
Item 56, References Cited, OTHER PUBLICATIONS, change "Lurna to --Luma"
Item 56, References Cited, OTHER PUBLICATIONS, change "LurnaCure" to --LumaCure--.

Column 1
Line 24, after "device" change "with" to --within--
Line 53, after "curing" change "it is" to --devices, battery powered light curing devices are--

Column 2
Line 17, change "includes" to --include--

Column 3
Line 58, change "(LEDs)" to --(LED)--

Column 4
Line 13, after "applicator" insert --12--
Line 67, change "10" to --unit 14--

Column 6
Line 21, change "fray" to --tray--

Signed and Sealed this

Twenty-fifth Day of July, 2006

JON W. DUDAS
*Director of the United States Patent and Trademark Office*